United States Patent
Zák et al.

(10) Patent No.: US 7,351,846 B2
(45) Date of Patent: Apr. 1, 2008

(54) OXALIPLATIN WITH A LOW CONTENT OF ACCOMPANYING IMPURITIES AND A METHOD FOR PREPARATION THEREOF

(75) Inventors: Frantisek Zák, Brno (CZ); Anna Czajka-Poulová, Ivancice (CZ)

(73) Assignee: Pliva-Lachema A.S., Brno (CZ)

( * ) Notice: Subject to any disclaimer, the term of this patent is extended or adjusted under 35 U.S.C. 154(b) by 0 days.

(21) Appl. No.: 10/595,286

(22) PCT Filed: Oct. 14, 2004

(86) PCT No.: PCT/CZ2004/000068

§ 371 (c)(1), (2), (4) Date: Apr. 5, 2006

(87) PCT Pub. No.: WO2005/035544

PCT Pub. Date: Apr. 21, 2005

(65) Prior Publication Data

US 2007/0073074 A1    Mar. 29, 2007

(30) Foreign Application Priority Data

Oct. 17, 2003 (CZ) ............................. PV 2855-03

(51) Int. Cl.
*C07F 15/00* (2006.01)
*A61K 31/28* (2006.01)

(52) U.S. Cl. ..................................... 556/137; 514/492

(58) Field of Classification Search ................ 556/137; 514/492

See application file for complete search history.

(56) References Cited

FOREIGN PATENT DOCUMENTS

JP        05-301884 A    * 11/1993

OTHER PUBLICATIONS

Chemical Abstracts, abstract No. 120:337782, abstract for JP 05-301884, 1994.*

* cited by examiner

*Primary Examiner*—Porfirio Nazario-Gonzalez
(74) *Attorney, Agent, or Firm*—Notaro & Michalos P.C.

(57) ABSTRACT

Oxaliplatin with a low content of accompanying impurities originating from its preparation which contains, by weight, at most 0.01%, preferably less than 0.001%, of alkali metals, at most 0.0005%, preferably less than 0.0002%, of silver, and at most 0.01%, preferably less than 0.001%, of nitrates. A method for preparation of the said oxaliplatin resides in that a suspension of (SP-4-2)-dichloro-[(1R,2R)-1,2-cyclohexanediamine-N,N']platinum(II) in water is treated with silver nitrate, then, after removal of the solid phase, the obtained solution is treated with quaternary ammonium iodide of the formula $(R)_4NI$, the separated solid phase is removed and the obtained solution is treated with oxalic acid, and the separated oxaliplatin is isolated, washed with water and a polar organic solvent or their mixture, dried, recrystallised from water, washed with water and polar organic solvent or their mixture, and dried.

3 Claims, No Drawings

OXALIPLATIN WITH A LOW CONTENT OF ACCOMPANYING IMPURITIES AND A METHOD FOR PREPARATION THEREOF

FIELD OF THE INVENTION

The invention concerns oxaliplatin with a low content of accompanying impurities originating from its preparation. The invention also concerns a method for preparation of this oxaliplatin by reacting (SP-4-2)-dichloro-[(1R,2R)-1,2-cyclo-hexanediamine-N,N']platinum(II) with silver nitrate, removing the solid phase, adding iodide ions, removing the solids, and reacting water solution of the corresponding diaqua complex of platinum with oxalic acid.

BACKGROUND OF THE INVENTION

Oxaliplatin is an international non-proprietary name for (SP-4-2)-[(1R,2R)-1,2-cyclohexandiamine-N,N']-(oxalato-O,O')-platinum(II) of the formula

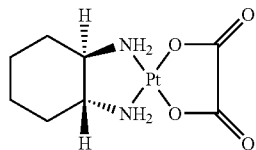

which is a platinum metalopharmacum showing antitumour activity against some malignant solid tumours, including particularly malignant tumours of colon and rectum.

The structure of oxaliplatin, its pharmaceutical properties, and method for preparation thereof are described, for example, in the U.S. Pat. No. 4,169,846, according to which a boiling aqueous solution of (SP-4-2)-dichloro-[(1R,2R)-1,2-cyclohexanediamine-N,N']platinum(II) is treated with 2 molar equivalents of an aqueous solution of a silver salt of a mineral acid, especially silver nitrate, protected from light. After cooling of the reaction mixture, the mixture is filtered repeatedly to obtain a clear filtrate, which filtrate is then concentrated under reduced pressure in order to get a concentrate containing diaqua complex of platinum. To the concentrate, a salt of dicarboxylic acid, such as potassium oxalate, is added in an equimolar amount in relation to the starting platinum(II) complex, and the obtained solution is allowed to stand at room temperature. Subsequently, the solution is further concentrated under reduced pressure to obtain white crystalline precipitate. The obtained precipitate containing the required oxaliplatin is recrystallised from water solution. This process gives relatively low yields and is laborious, especially due to the fact that it is necessary to concentrate high volumes of filtrate and reaction mixture in individual steps. For this reason, the process is not suitable for carrying out on industrial scale. In the said patent document purity of oxaliplatin is not specified, particularly concerning the accompanying impurities originating from the process of preparation thereof, and the document does not state that the oxaliplatin obtained in this way would be suitable as an active compound for the preparation of pharmaceutical compositions, either.

The U.S. patent document No. U.S. Pat. No. 5,290,961 describes, inter alia, a method for preparation of oxaliplatin free or unreacted silver ions. According to this method, a platinum complex where platinum has the oxidation number II and which contains 1,2-cyclohexanediamine ligand and halogen ligands, is treated with a solution of at least two equivalents of silver. Subsequently, the precipitate of silver chloride or bromide is removed and a solution of sodium iodide or potassium iodide is added to the remaining solution, in order to convert the unreacted starting platinum compound, by-products of the starting compound and unreacted silver ion into insoluble form of iodine compounds, which are then removed, and, subsequently, a dibasic organic acid is added to the remaining solution of platinum complex. This method represents the last steps of a modified Dhar synthesis, according to which the starting compound is converted into a complex comprising iodine by the treatment with alkali metal iodide, then, after conversion into a relevant complex, the complex is treated with a soluble silver salt, and, subsequently, after removal of insoluble portion which contains essentially all present impurities including silver iodide, the produced aqua complex is converted into the corresponding product.

The international patent application No. WO 03/004505 describes oxaliplatin which can be used as a pharmacologically active compound. According to the said application, oxaliplatin is prepared in several steps: Initially potassium tetrachloroplatinate(II) is reacted with trans-(+)-1,2-cyclohexanediamine to obtain dichloro-(trans-(+)-1,2-cyclohexanediamine)-platinum(II), which is, after suspending in water, treated with a solution of silver nitrate in an amount of 2 equivalents in relation to the said platinum(II) complex, wherein a solution of potassium or sodium iodide and activated charcoal is optionally added to the obtained solution under stirring. After filtration, an alkali metal salt of oxalic acid is added to the filtrate, crystals of oxaliplatin are filtered off and washed up to five times with water having a pH 4.5 to 7.0. Oxaliplatin is purified by recrystallisation and crystals of oxaliplatin are collected on a filter, washed up to five times with water having a pH of 4.5 to 7.0. Although oxaliplatin is only slightly soluble in water at room temperature, it is obvious from Example 1 of said international patent application that washing with water causes losses of about 20% of oxaliplatin in one single operation only, i.e. during recrystallisation. This is a substantial drawback of this method for preparation of oxaliplatin.

Therefore, the purpose of the invention is to provide a method for preparation of a highly pure oxaliplatin, which method would be free of the drawbacks mentioned above.

SUMMARY OF THE INVENTION

To achieve the purpose described above, the invention provides oxaliplatin with a low content of accompanying impurities originating from its preparation, characterized in that it contains, by weight, at most 0.01%, preferably less than 0.001%, of alkali metals, at most 0.0005%, preferably less than 0.0002%, of silver, and at most 0.01%, preferably less than 0.001%, of nitrates.

A further subject of the invention is a method for preparation of oxaliplatin described above, by reacting (SP-4-2)-dichloro-[(1R,2R)-1,2-cyclohexanediamine-N,N']platinum(II) with silver nitrate, removing the solid phase, adding iodide ions, removing the solids, and reacting the aqueous solution of the corresponding diaqua complex of platinum with oxalic acid, the method being characterized in that a suspension of (SP-4-2)-dichloro-[(1R,2R)-1,2-cyclohexanediamine-N,N']platinum(II) in water is treated with silver nitrate in a molar ratio of the complex to silver nitrate of 1:≦2, then, after removal of the solid phase, the obtained solution is treated with quaternary ammonium iodide of the formula $(R)_4NI$, wherein each R independently represents hydrogen atom, optionally substituted aliphatic radical containing 1 to 10 carbon atoms, or optionally substituted cycloaliphatic radical containing 3 to 10 carbon atoms, with the proviso that at least one of the symbols R does not represent hydrogen atom, the separated solid phase is removed and the obtained solution is treated with oxalic acid, and the separated oxaliplatin is isolated, washed with water and a polar organic solvent or their mixture, dried, recrystallised from water, washed with water and polar organic solvent or their mixture, and dried. The polar solvent used in the method is preferably an aliphatic alcohol containing 1 to 4 carbon atoms, especially ethanol.

The whole synthesis of oxaliplatin according to the invention is preferably carried out at room temperature, in view of the fact that such synthesis requires the lowest energy consumption. The preparation of the aqua complex, its purification and the synthesis of oxaliplatin itself at increased temperature requires, in addition to the supply of heat during these steps, also cooling before the steps of separation of impurities, accompanying compounds, by-products and the final product itself. Increased temperature results in increase of the amount of impurities and by-products in the reaction mixture. To the contrary, lower temperatures disproportionately lengthen the reaction time. The individual reaction components, i.e. silver nitrate, ammonium iodide and oxalic acid, used usually in the form of dihydrate, are preferably used as solid compounds, because, in such case, the synthesis gives higher yields and it is not necessary to concentrate the obtained solution of (SP-4-2)-diaqua-[(1R,2R)-1,2-cyclohexanediamine-N,N'] platinum(II), and, optionally, also the reaction mixture during the synthesis of oxaliplatin itself. Such concentrating is a source of impurities and by-products. The use of polar solvent for washing of both the synthesised and recrystallised oxaliplatin facilitates removal of the residual reaction components, and, optionally, also the accompanying by-products, from the final product, wherein oxaliplatin is essentially insoluble in ethanol. The use of the stated system of washing of oxaliplatin during isolation thereof, both after synthesis thereof and after recrystallisation thereof, is possible also because of the fact that in reactions during which the diaqua complex is purified, and in synthesis of oxaliplatin itself, agents which do not contain alkali metals are used. The reaction components mentioned above are used in an excess, in relation to stoichiometry of the equations defining chemical reactions of the formation of the aqua complex, purification thereof, and the oxaliplatin synthesis. Silver nitrate is usually used in an excess of 1 molar %, and quaternary ammonium iodide is used the an excess of 10 molar %. A further increase of the consumption amounts of the above agents results in gradual decrease of yields of the individual steps, wherein the oxaliplatin quality does not change significantly. During synthesis of oxaliplatin, it seems preferable to use oxalic acid in about stoichiometric amount, relating to the starting (SP-4-2)-dihalogen-[(1R, 2R)-1,2-cyclohexanediamine-N,N ']platinum(II).

The method according to the invention yields very pure oxaliplatin which can be used as a pharmacologically active compound in pharmaceutical composition. This was not obvious from the state of the art.

In the following part of the description, the invention is explained in greater detail by means of an example of a specific embodiment thereof. The example is given solely for illustrative purpose, and does not limit the scope of the invention in any way. The scope of the invention is defined by the claims and the description.

EXAMPLE

Silver nitrate (80.6 g) is added to a suspension of 88.9 g of (SP-4-2)-dichloro-[(1R,2R)-1,2-cyclohexanediamine-N, N']platinum(II) in 900 ml of water, and the obtained mixture is stirred for 70 hours at room temperature, in the dark. The insoluble portion is filtered off of the reaction mixture, and this portion is washed with 100 ml of water. Tetraethylammonium (2.5 g) iodide is added to the filtrate mixed with the washing liquid, and the obtained mixture is stirred for 16 hours. Activated charcoal (0.6 g) is added to the reaction mixture, and the mixture is filtered. Oxalic acid dihydrate (29.5 g) is added to the obtained filtrate under stirring, and 4 hours later the precipitated oxaliplatin is filtered off. The filter cake is washed with 30 ml of water and 500 ml of ethanol divided into five portions, and the raw product is dried in a vacuum drier. After recrystallisation from water, the separated oxaliplatin is washed with 30 ml of water and 400 ml of ethanol divided into five portions, and dried in a vacuum drier at 70° C. up to a constant weight. Oxaliplatin is obtained in a yield of 50.2 g (54% of the theoretical yield based on the starting (SP-4-2)-dichloro-[(1R,2R)-1,2-cyclohexanediamine-N,N']platinum(II). The obtained oxaliplatin contains less than 0.001% by weight of alkali metals, less than 0.0002% by weight of silver, and less than 0.001% of nitrates ($NO_3^-$). The content of oxalic acid is lower than 0.01% by weight.

A further advantage of the method is that oxaliplatin prepared by the method according to the invention essentially does not contain either the starting (SP-4-2)-dichloro-[(1R,2R)-1,2-cyclohexanediamine-N,N ]platinum(II), as proved by high performance liquid chromatography (HPLC) analysis (the content of chlorine in oxaliplatin is lower than 0.0001% by weight), or any by-products.

The invention claimed is:

1. A method for preparation of oxaliplatin with a low content of accompanying impurities originating from its preparation, characterized in that the oxaliplatin contains, by weight, at most 0.01% of alkali metals, at most 0.0005% of silver, and at most 0.01% of nitrates, the method comprising: reacting (SP-4-2)-dichloro-[(IR, 2R)-1, 2-cyclo- hexanediamine-N, N'] platinum (II) with silver nitrate, removing the solid phase, adding iodide ions, removing the solids, and reacting the aqueous solution of the corresponding diaqua complex of platinum with oxalic acid, characterized in that a suspension of (SP-4-2)-dichloro-[(IR, 2R)-1, 2-cyclohexanediamine-N, N] platinum (II) in water is treated with silver nitrate in a molar ratio of the complex to silver nitrate of 1:<2 then, after removal of the solid phase, the obtained solution is treated with quaternary ammonium iodide of the formula (R) 4NI wherein each R independently represents hydrogen atom, or aliphatic radical containing 1 to 10 carbon atoms, or cycloaliphatic radical containing 3 to 10 carbon atoms, with the proviso that at least one of the symbols R does not represent hydrogen atom, the separated solid phase is removed and the obtained solution is treated with oxalic acid, and the separated oxaliplatin is isolated, washed with water and a polar organic solvent or their mixture, dried, recrystallised from water, washed with water and polar organic solvent or their mixture, and dried.

2. The method according to claim 1, characterized in that an aliphatic alcohol containing 1 to 4 carbon atoms is used as the polar solvent.

3. The method according to claim 1, characterized in that ethanol is used as the polar solvent.

* * * * *